United States Patent [19]

Ramachandran

[11] Patent Number: 4,539,397

[45] Date of Patent: Sep. 3, 1985

[54] (ALKOXYDIAZO)HALOBENZENEACETONITRILES

[75] Inventor: Venkataraman Ramachandran, Baton Rouge, La.

[73] Assignee: Ethyl Corporation, Richmond, Va.

[21] Appl. No.: 635,215

[22] Filed: Jul. 27, 1984

Related U.S. Application Data

[62] Division of Ser. No. 488,068, Apr. 25, 1983.

[51] Int. Cl.$^3$ .................. C07C 113/00; C07C 120/00; C07C 121/66; C07C 121/68
[52] U.S. Cl. ............................... 534/556; 260/465 D; 260/465 E; 260/465 F; 260/465 G; 534/565
[58] Field of Search .................... 260/141 AN, 141 R; 534/556

[56] References Cited

U.S. PATENT DOCUMENTS 3,300,471 1/1967 Arrigo .................................. 260/142
3,992,409 11/1976 Utne et al. ........................... 260/649

FOREIGN PATENT DOCUMENTS 57-16830 1/1982 Japan ................................... 260/649
2065655 7/1981 United Kingdom ................ 260/649

OTHER PUBLICATIONS

Hassanaly et al., Bull. Soc. Chim. France, volume of 1974, pp. 560 to 562.
Vernin, Bull. Soc. Chim. France, volume of 1974, pp. 1079 to 1084.

*Primary Examiner*—Floyd D. Higel
*Attorney, Agent, or Firm*—Donald L. Johnson; John F. Sieberth; Patricia J. Hogan

[57] ABSTRACT

The coupling of an aminohalobenzeneacetonitrile with a benzene compound in the presence of an alkyl nitrite to form a halobiphenylacetonitrile via a diazo intermediate is improved by conducting the reaction at a temperature of about 0°–15° C. until diazotization of the aminohalobenzeneacetonitrile is substantially complete. Use of the low diazotization temperature leads to an increased yield of halobiphenylacetonitrile.

2 Claims, No Drawings

(ALKOXYDIAZO)HALOBENZENEACETONITRILES

This application is a division of application Ser. No. 488,068, filed Apr. 25, 1983.

TECHNICAL FIELD

This invention relates to halobiphenylacetonitriles and more particularly to an aryl coupling process for preparing them.

BACKGROUND

As disclosed in U.K. patent application No. 2 065 655 A (Upjohn) and Japanese Kokai Patent Application No. SHO-57[1982]-16830 (Sagami), it is known to prepare halobiphenyl compounds by pseudo-Gomberg reactions wherein an aminohalobenzene is diazotized with an alkyl nitrite and then coupled with a benzene compound. Except when a copper catalyst has been employed, these reactions have typically utilized elevated diazotization temperatures, e.g., 20°–80° C., preferably about 65° C., although (1) U.S. Pat. No. 3,992,459 (Utne et al.) shows that lower diazotization temperatures can be used for such reactions when the amine has been protonated before being contacted with the alkyl nitrite and a catalyst is employed, and (2) the use of lower diazotization temperatures for the reactions between non-halogenated aromatic amines and isoamyl nitrite is disclosed in Hassanaly et al., Bull. Soc. chim., 1974, pp. 560–562, and Vernin et al., Bull. Soc. chim., 1974, pp. 1079–1084.

A variety of haloaminobenzenes is taught to be utilizable in the Upjohn processes, including compounds having a cyano group attached to the aromatic ring. However, the amino compounds of the working examples are limited to dihaloanilines, and Upjohn does not suggest how their teachings could be modified to permit an efficient coupling of benzene compounds and substituted aminohalobenzenes outside the scope of their invention, such as aminohalobenzenes having a cyano group indirectly attached to the aromatic ring through an alkyl group. Such substituted aminohalobenzenes have been found to lead to much lower yields of biphenyl compounds than the aminobenzenes taught by Upjohn.

Sagami prophetically teaches that aminohalobenzeneacetonitriles may be used in their aryl coupling processes but—like Upjohn—do not suggest how the teachings of their working examples could be modified to permit an efficient coupling of such compounds with benzene compounds, and particularly do not suggest how such an efficient coupling could be accomplished in the absence of a copper catalyst.

SUMMARY OF INVENTION

An object of this invention is to provide a novel aryl coupling process for preparing halobiphenylacetonitriles.

Another object is to provide such a process which leads to higher yields of halobiphenylacetonitriles.

A further object is to provide such a process wherein the halobiphenylacetonitriles are prepared via novel diazo intermediates.

These and other objects are attained by using a diazotization temperature of about 0°–15° C. in a pseudo-Gomberg process for coupling an aminohalobenzeneacetonitrile with a benzene compound. Specifically, in a process for coupling an aminohalobenzeneacetonitrile with a benzene compound in the presence of an alkyl nitrite to form a halobiphenylacetonitrile via a diazo intermediate, the invention resides in the improvement of conducting the reaction at a temperature of about 0°–15° C. until diazotization of the aminohalobenzeneacetonitrile is substantially complete.

DETAILED DESCRIPTION

Aminohalobenzeneacetonitriles utilizable in the practice of the invention are anilines having at least one halo substituent and at least one acetonitrile substituent on the aromatic ring. The halo substituents may be bromo, chloro, iodo, or fluoro; and the acetonitrile substituents may be any group corresponding to the formula:

wherein R is hydrogen or an alkyl group, generally an alkyl group of 1–6 carbons. A preferred aminohalobenzeneacetonitrile is 2-(4-amino-3-fluorobenzene)propionitrile, which is ideally suited for the preparation of 2-(2-fluoro-4-biphenyl)propionitrile, a flurbiprofen intermediate, by the process of the invention.

Benzene compounds which can be used in the process of the invention are benzene itself and substituted benzenes bearing 1–5 substituents, such as hydroxy, halo, nitro, alkyl, alkoxy, alkoxycarbonyl, aryloxycarbonyl, phenyl, cyano, or cycloalkyl substituents—any organic substituents generally containing not more than about 10, preferably not more than 4, carbons. The preferred benzene compound is benzene itself. Since this component of the reaction mixture functions as a solvent as well as a reactant, and the amount used may affect the yield of product obtainable, it is employed in excess of the amount required to couple with the aminohalobenzeneacetonitrile. Generally, the amount of benzene compound employed is in the range of about 10–300, preferably about 50–150, mols per mol of aminohalobenzeneacetonitrile.

The alkyl nitrite used to diazotize the aminohalobenzeneacetonitrile may be any of the alkyl nitrites commonly employed in pseudo-Gomberg reactions, generally an alkyl nitrite containing 1–6 carbons, such as the n-butyl, isobutyl, t-butyl, isoamyl, and isopropyl nitrites. The amount of alkyl nitrite that should be employed varies with the degree of dilution of the reaction mixture, larger amounts generally being required when the reaction is more dilute. However, it is an advantage of the invention that the process usually requires less alkyl nitrite than comparable processes conducted at higher diazotization temperatures, so an alkyl nitrite concentration as low as about 1.0–1.5 mol per mol of aminohalobenzeneacetonitrile is frequently satisfactory. As a rule, the amount of alkyl nitrite employed is in the range of about 1–5 mols per mol of aminohalobenzeneacetonitrile.

The process of the invention may be conducted in the absence of a catalyst but is speeded by the use of a catalytic amount, e.g., about 1–8 mol % (based on the amount of aminohalobenzeneacetonitrile) of an acid. Acids that can be employed as catalysts include inorganic acids, such as sulfuric, hydrochloric, etc., and organic acids, such as benzoic, chloroacetic, dichloroacetic, trichloroacetic, methanesulfonic, acetic, etc.

In addition to the aforementioned ingredients, the reaction mixture may also contain other optional ingredients, such as finely-divided inert solids capable of absorbing water, e.g., anhydrous magnesium sulfate, silica gel, diatomaceous earth, etc.

The diazotization of the invention is conducted at a temperature of about 0°–15° C., preferably about 5°–10° C. Use of such temperatures results in increasing the yield of product obtainable by the overall coupling process. When the diazotization is substantially complete, coupling of the diazo intermediate and the benzene compound may be accomplished under conventional conditions, typically at reflux temperatures.

The diazo intermediates formed in the process of the invention are novel compounds corresponding to the formula:

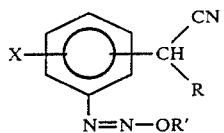

wherein R is hydrogen or an alkyl group (generally an alkyl group of 1–6 carbons), R' is the alkyl residue of the alkyl nitrite (also generally an alkyl group of 1–6 carbons), and X is halo, i.e., bromo, chloro, iodo, or fluoro. These compounds usually have the acetonitrile and halo substituents in positions which are, respectively, para and ortho to the diazo group. For example, when the aminohalobenzene starting material is 2-(4-amino-3-fluorobenzene)propionitrile, the novel diazo intermediate corresponds to the formula:

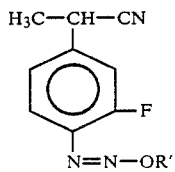

The following examples are given to illustrate the invention and are not intended as a limitation thereof. Unless otherwise specified, yields given in these examples are yields determined by VPC analysis.

EXAMPLE I

A solution of one molar proportion of AFPN in 4.6 molar proportions of benzene was cooled to 0°–5° C., a solution of 1.1 molar proportions of isoamyl nitrite in 4.6 molar proportions of benzene was slowly added thereto with constant stirring, and stirring was continued for one hour. Another 0.4 molar proportion of isoamyl nitrite was added, followed by 46 molar proportions of benzene; and the reaction mixture was then refluxed for 5.5 hours and subsequently worked up to isolate the product. The reaction resulted in a 48% yield of FBPN.

EXAMPLE II

A solution of one molar proportion of AFPN in 92 molar proportions of benzene was cooled to 5°–10° C. and stirred, 1.5 molar proportions of isoamyl nitrite were added, and stirring was continued for one hour. Then the reaction mixture was heated on a 90° C. bath for 22 hours and subsequently worked up to isolate the product. The reaction resulted in a 64% yield of FBPN.

EXAMPLE III

A solution of one molar proportion of AFPN in 88 molar proportions of benzene was cooled to 5°–10° C. and stirred, 1.5 molar proportions of isoamyl nitrite were added, and the mixture was stirred under nitrogen for 60–90 minutes. It was then heated on a 90° C. bath for 22 hours under nitrogen and subsequently worked up to isolate the product. The reaction resulted in a 60% yield of FBPN.

EXAMPLE IV

A solution of one molar proportion of AFPN and 0.08 molar proportion of AFPN hydrochloride in 100 molar proportions of benzene was cooled to 5°–10° C., one molar proportion of isoamyl nitrite was quickly added thereto, and stirring at 5°–10° C. was continued for one hour, after which another 0.5 molar proportion of isoamyl nitrite was added. After three hours, the mixture was heated on a 90° C. bath, where it was kept for 18 hours and then worked up to isolate the product. The reaction resulted in a 47% yield of FBPN.

EXAMPLE V

Example IV was repeated except that only 0.01 molar proportion of AFPN hydrochloride was employed, the second charge of nitrite was made after the reaction mixture containing the first nitrite charge had been stirred at 5°–10° C. for 90 minutes, and the reaction mixture was then maintained at that temperature for an additional five hours before the temperature was raised. The reaction resulted in a 57% yield of FBPN.

In another 65 pseudo-Gomberg reactions, 42 of which were conducted in accordance with the present invention, and 23 of which were conducted by comparable processes utilizing higher diazotization temperatures, the processes of the invention led to an average FBPN yield of 45%, whereas the other processes led to an average FBPN yield of 32%.

I claim:

1. A diazo compound corresponding to the formula:

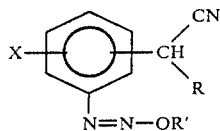

wherein R is hydrogen or an alkyl group, R' is an alkyl group, and X is halo.

2. A diazo compound corresponding to the formula:

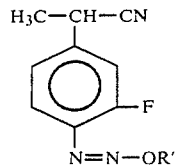

wherein R' is an alkyl group of 1–6 carbons.

* * * * *